US00PP10625P

United States Patent [19]

Holtkamp, Sr.

[11] Patent Number: Plant 10,625

[45] Date of Patent: Sep. 29, 1998

[54] AFRICAN VIOLET PLANT NAMED 'IMPROVED HAWAII'

[75] Inventor: Reinhold Holtkamp, Sr., Rees-Haffen, Germany

[73] Assignee: International Plant Breeding A.G., Bern, Switzerland

[21] Appl. No.: 798,295

[22] Filed: Feb. 7, 1997

[51] Int. Cl.[6] ..... A01H 5/00

[52] U.S. Cl. ..... Plt./69.2

[58] Field of Search ..... Plt./69.2

*Primary Examiner*—James R. Feyrer

*Assistant Examiner*—Melissa L. Kimball

*Attorney, Agent, or Firm*—Foley & Lardner

[57] ABSTRACT

A new and distinct cultivar of African violet named Improved Hawaii, as described and illustrated, and particularly characterized by its single to semi-double, star-shaped, purplish blue flowers with fine white wavy edges; strong, upright flower stems that curve slightly toward the center to form a compact bouquet above the leaves; dark green, oval to heart-shaped, slightly serrated leaves; profuse flowering; vigorous and compact growth habit; flowering 9–10 weeks after potting, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Improved Hawaii.

The new cultivar was referred to during the breeding and selection process by the designation 101/41 and is a product of a planned breeding program. The new cultivar was originated from a cross made by me in the controlled breeding program in Haffen, Federal Republic of Germany. The female, or seed parent was a cultivar designated 96. The male, or pollen parent was a cultivar designated 1041.

Improved Hawaii was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Improved Hawaii has not ben observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Improved Hawaii, which in combination distinguish this African violet as a new and distinct cultivar:

(1) Spring, upright flower stems curving slightly toward the center.

(2) Single to semi-double star-shaped, purplish blue flowers with fine white wavy edges.

(3) Profuse flowering.

(4) Each plant carries (10–12 and more upright flower stems each of which carries 5–7 and more flowers.

(5) Long lasting, non-dropping flowers.

(6) Vigorous and compact grower.

(7) Plant saleable 9 to 10 weeks after potting.

(8) Seed capsules push slightly through.

(9) Dark green, oval to heart-shaped, slightly serrated leaves.

(10) After maturity the flowers dry off, and remain on the peduncle without becoming infected by botrytis.

The new cultivar is most similar to, and was specifically intended to improve upon the characteristics of, my previoulsy patented cultivar Hawaii (U.S. Plant Pat. No. 4,546). In comparison to Hawaii, the new cultivar is principally distinguished by its more compact growth habit (both in height and size), single to semi-double petals (1 to 5 extra little petals), rounder petals and by its better blooming habit.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn.

Botanical classification: *Saintpaulia ionantha,* Ramat., c.v. Improved Hawaii.

Parentage:

*Male parent.*—104.

*Female parent.*—96.

Propagation: The new cultivar holds its distinguishing characteristics through successive propagations by leaf cuttings.

Plant: From 9 cm to 11 cm tall when grown in pots, and 24–28 cm in diameter when fully grown.

*Leaves.*—General form:Oval to heart-shaped. Diameter: 60–70 mm wide and 75–85 mm long. Texture: Velvety. Aspect: Slightly serrated, hairy, slightly shiny. Veins: Upperside: visible; underside: well pronounced, light green, shiny; on young leaves purplish red. Color (upperside): Yellow-Green Group147 A and somewhat darker. Color (underside): Greyed-Purple Group 186 A. Petiole: Strong, purplish brown, hairy.

*Flowers.*—Buds: Bell-shaped, light green with purplish blue touch. 5–7 mm just before opening. Sepals: Five (5). Color: Purplish brown. Calyx: Shape: Funnel-shaped. Aspect: Spear-shaped, hairy. Peduncle: Character: Strong upright, hairy. Color: Purplish brown.

*Individual flowers.*—Size: 40–45 mm. Shape: Star-shaped, single to semi-double (having 1–5 extra small petals) with wavy edges. Color (upperside): Violet-Blue Group 89 B to C with fine white edges.

Under cooler temperatures and more intensive lighting, the purplish blue tends to intensify. Color (underside): Violet Group 88 B to C. Borne: Each flower stem carries 5–7 and more flowers on strong, upright peduncles that are free standing above the leaves, thereby forming a compact bouquet. Flowering habit: Flowers 9–10 weeks after potting.

*Reproductive Organs.*—Stamens: Five (5) Anthers: 5 composed of 10 anther cells, seed capsules push slightly through. Filaments: Yellowish white, 3–4 mm long. Pollen Color: Yellow Group 7 A. Styles: 7–8 mm long, purplish blue, base of ovary light green and hairy.

*Roots.*—Normally developed, white when young, turning slightly brownish when older.

Disease resistance: Up to date, Improved Hawaii has shown very good resistance to all major violet diseases.

General Observations:

Improved Hawaii is an attractive cultivar due to its star-shaped, purplish blue flowers contrasting nicely with the bright yellow anthers. The blossoms have fine white wavy edges and 1 to 5 extra small petals which give Improved Hawaii a single to semi-double appearance. A tight bouquet of flowers free standing above the leaves develops 9–10 weeks after potting. Each of the 10–12 and more strong flower stems carries 5–7 and more flowers. Dark green, oval to heart-shaped, slightly serrated leaves surround the flower bouquet. The flowers are long-lasting and non-dropping and the seed capsules push slightly through.

I claim:

1. A new and distinct cultivar of African violet plant named Improved Hawaii, as described and illustrated, and particularly characterized by its single to semi-double, star-shaped, purplish blue flowers with fine white wavy edges; strong, upright flower stems that curve slightly toward the center to form a compact bouquet above the leaves; dark green, oval to heart-shape, slightly serrated leaves; profuse flowering; vigorous and compact growth habit; flowering 9–10 weeks after potting, and by its long lasting and non-dropping flowers.

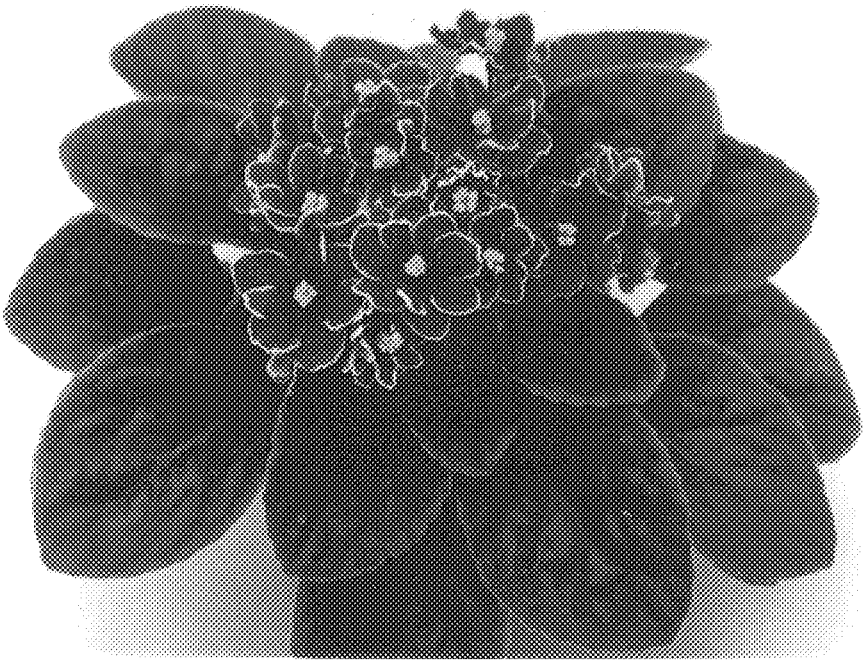

* * * * *